United States Patent
Sun et al.

(10) Patent No.: US 12,150,744 B2
(45) Date of Patent: Nov. 26, 2024

(54) SENSOR SYSTEM AND SENSING METHOD FOR USE IN ASSESSMENT OF CIRCULATORY VOLUME

(71) Applicant: KONINKLIJKE PHILIPS N.V., Eindhoven (NL)

(72) Inventors: Shaoxiong Sun, Eindhoven (NL); Wouter Herman Peeters, Waalre (NL); Rick Bezemer, Utrecht (NL); Xi Long, Eindhoven (NL); Ronaldus Maria Aarts, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 1280 days.

(21) Appl. No.: 16/651,568

(22) PCT Filed: Sep. 18, 2018

(86) PCT No.: PCT/EP2018/075137
§ 371 (c)(1),
(2) Date: Mar. 27, 2020

(87) PCT Pub. No.: WO2019/063349
PCT Pub. Date: Apr. 4, 2019

(65) Prior Publication Data
US 2020/0260967 A1      Aug. 20, 2020

(30) Foreign Application Priority Data
Sep. 27, 2017   (EP) .................................. 17193449

(51) Int. Cl.
*A61B 5/026*   (2006.01)
*A61B 5/00*   (2006.01)
(Continued)

(52) U.S. Cl.
CPC ........ *A61B 5/0261* (2013.01); *A61B 5/02433* (2013.01); *A61B 5/029* (2013.01);
(Continued)

(58) Field of Classification Search
CPC ... A61B 5/0261; A61B 5/02433; A61B 5/029; A61B 5/0295; A61B 5/6814;
(Continued)

(56) References Cited

U.S. PATENT DOCUMENTS

| | | |
|---|---|---|
| 9,855,012 B2 | 1/2018 | Banerjee |
| 2003/0166996 A1 | 9/2003 | Kim et al. |

(Continued)

FOREIGN PATENT DOCUMENTS

| | | |
|---|---|---|
| JP | 2013202123 A | 10/2013 |
| WO | 2014176335 A1 | 10/2014 |

(Continued)

OTHER PUBLICATIONS

International Search Report and Written Opinion, International Application No. PCT/EP2018/075137, Mailed on Oct. 29, 2018.

(Continued)

*Primary Examiner* — Eric F Winakur
*Assistant Examiner* — Abid A Mustansir

(57) ABSTRACT

In a sensor system (12), output signals of at least one PPG sensor (14) are processed to derive a modified pulse amplitude variation (PAV) value, being modified to take account of a baseline variation of the PPG sensor output signal. In particular, the modified PAV is derived through performing a modification step (42) in which either: a baseline variation of the PPG sensor output is derived and combined with a previously derived PAV, or, a PPG sensor output is first processed to perform baseline variation compensation, in advance of then deriving a PAV from the compensated signal.

20 Claims, 3 Drawing Sheets

(51) Int. Cl.
  *A61B 5/024* (2006.01)
  *A61B 5/029* (2006.01)
  *A61B 5/0295* (2006.01)
  *A61B 5/1455* (2006.01)

(52) U.S. Cl.
  CPC .......... *A61B 5/0295* (2013.01); *A61B 5/6814* (2013.01); *A61B 5/6826* (2013.01); *A61B 5/725* (2013.01); *A61B 5/7278* (2013.01); *A61B 5/14552* (2013.01)

(58) Field of Classification Search
  CPC ..... A61B 5/6826; A61B 5/725; A61B 5/7278; A61B 5/14552
  See application file for complete search history.

(56) References Cited

U.S. PATENT DOCUMENTS

| | | |
|---|---|---|
| 2011/0270097 A1 | 11/2011 | Aboy |
| 2014/0073867 A1 | 3/2014 | Rodriguez-Llorente et al. |
| 2014/0323822 A1* | 10/2014 | Addison .............. A61B 5/0295 600/301 |
| 2014/0323824 A1 | 10/2014 | Addison |
| 2015/0265196 A1 | 9/2015 | Su et al. |
| 2016/0073965 A1 | 3/2016 | Addison et al. |

FOREIGN PATENT DOCUMENTS

| | | |
|---|---|---|
| WO | 2014176577 A1 | 10/2014 |
| WO | 2015107268 A1 | 7/2015 |
| WO | 2016097935 A1 | 6/2016 |
| WO | 2017100188 A2 | 6/2017 |

OTHER PUBLICATIONS

Leier, M. et al., "Respiration signal extraction from photoplethysmogram using pulse wave amplitude variation", 2014 IEEE International Conference on Communications, pp. 3535-3540.

Shelley, K. et al., "What Is the Best Site for Measuring the Effect of Ventilation on the Pulse Oximeter Waveform?", Aug. 2006, vol. 103, Issue 2.

Hengy B, Gazon M, Schmitt Z, et al. Oximetry Plethysmographic Waveform Amplitude and. 2012;(5):973-980.

Landsverk SA, Hoiseth LO, Kvandal P, Hisdal J, Skare O, Kirkeboen K a. Poor agreement between respiratory variations in pulse oximetry photoplethysmographic waveform amplitude and pulse pressure in intensive care unit patients. Anesthesiology. 2008;109(5):849-855. doi:10.1097/ALN.0b013e3181895f9f.

Høiseth LØ, Hoff IE, Skare O, Kirkebøen K a, Landsverk S a. Photoplethysmographic and pulse pressure variations during abdominal surgery. Acta Anaesthesiol Scand. 2011;55(10):1221-1230. doi: 10.1111/j.1399-6576.2011.02527.x.

Addison PS, Wang R, Uribe AA, Bergese SD. Increasing signal processing sophistication in the calculation of the respiratory modulation of the photoplethysmogram (DPOP). J Clin Monit Comput. 2015;29(3):363-372. doi:10.1007/s10877-014-9613-3.

Alian, A et al., "Ventilation-Induced Modulation of Pulse Oximeter Waveforms: A Method for the Assessment of Early Changes in Intravascular Volume During Spinal Fusion Surgery in Pediatric Patients", Anesthesia & Analgesia: Aug. 2016—vol. 123—Issue 2—p. 346-356.

Cannesson, M. et al., "Pleth variability index to monitor the respiratory variations in the pulse oximeter plethysmographic waveform amplitude and predict fluid responsiveness in the operating theatre", British Journal of Anaesthesia 101 (2): 200-6 (2008).

* cited by examiner

SENSOR SYSTEM AND SENSING METHOD FOR USE IN ASSESSMENT OF CIRCULATORY VOLUME

This application is the U.S. National Phase application under 35 U.S.C. § 371 of International Application No. PCT/EP2018/075137, filed on 18 Sep. 2018, which claims the benefit of European Application Serial No. 17193449.0, filed 27 Sep. 2017. These applications are hereby incorporated by reference herein.

FIELD OF THE INVENTION

The present invention relates to a sensor system and method for use in assessment of circulatory volume.

BACKGROUND OF THE INVENTION

Circulatory volume is the total volume of arterial blood present in the circulatory system, and effectively perfusing tissue in the body, at any given time. Optimal circulatory volume status is important for patients in the operating room (OR) and the intensive care unit (ICU). Hypovolemia is a state of decreased blood volume and can lead to inadequate oxygen delivery to tissues. Hypervolemia is a state of fluid overload in the blood and can induce tissue edema and oxygen delivery alteration. Hemodynamic optimization, with the aim of providing optimal circulatory volume, has been shown to be able to improve postoperative outcome and reduce the cost of the surgery.

Unfortunately, circulatory volume status cannot be assessed directly. Fluid responsiveness has been used as an indirect assessment of volume status. It aims to determine if a patient's cardiac output, and hence hemodynamics, can be improved by giving fluid. Extra fluid loading may cause complications and hence has to be avoided in some situations. To evaluate fluid responsiveness, static indicators and dynamic indicators have been proposed.

Static indicators include for instance central venous pressure (CVP) and left ventricular end-diastolic area. However, these have been demonstrated to have poor performance for assessing fluid responsiveness.

Dynamic indicators, relying on cardiopulmonary interactions, have been shown to be better predictors for patients undergoing mechanical ventilation. Mechanical ventilation induces cyclic changes in the intrathoracic pressure (i.e., the external pressure on the heart muscle). The cyclic changes in the intrathoracic pressure can induce cyclic changes in the preload of the heart (the end-diastolic blood volume inside the heart). The cyclic changes in the preload can induce cyclic changes in the stroke volume of the heart, which will appear as cyclic changes in the pulse pressure.

If the cyclic changes in the intrathoracic pressure result in sufficiently strong cyclic changes of the stroke volume, the patient is predicted to be fluid responsive. If the cyclic changes in the intrathoracic pressure do not result in sufficiently strong cyclic changes of the stroke volume, the patient is predicted not to be fluid responsive.

Measurement of pulse pressure variation (PPV) is designed to quantify the cyclic changes in the pulse amplitude of a hemodynamic waveform. PPV is originally defined on the arterial blood pressure (ABP) signal:

$$PPV\ (\%) = 100 \times \{(PPmax - PPmin)/([PPmax + PPmin]/2)\}$$

where PP refers to the pulse pressure. This is hence effectively a measure of variation in pulse pressure, divided by average pulse pressure.

During positive pressure ventilation, pulse pressure increases with inspiration and decreases with expiration. PPV has been shown to be useful for mechanically ventilated patients with acute circulatory failures related to sepsis, and for patients who have undergone coronary artery bypass grafting. In general, the application of PPV has been proven to decrease the length of stay in hospital.

The derivation of PPV is often associated with catheterization, which may lead to clinical complications. Thus, pulse amplitude variation (PAV), derived from photoplethysmography (PPG), has been proposed as a surrogate. It is precisely defined as:

$$PAV\ (\%) = 100 \times \{(PAmax - PAmin)/([PAmax + PAmin]/2)\}$$

where PA refers to the pulse amplitude of the PPG signal.

PPG sensors provide a non-invasive measurement approach, for measuring volumetric changes of a body.

In summary, (PPG measured) PAV provides a non-invasive surrogate for PPV. PPV provides an indication of cyclic changes in the stroke volume of the heart, which in turn indicates the degree to which cyclic changes in the intrathoracic pressure caused by mechanical ventilation are affecting pre-load of the heart. Where the effect on pre-load is great, this indicates fluid responsiveness. The contrary indicates low fluid responsiveness. Hence, it follows that monitoring PAV signal can provide a non-invasive indication of fluid responsiveness.

A pulse oximeter is a common example of a PPG-based sensor. The purpose of pulse oximetry is to monitor the oxygen saturation of a patient's blood. While the purpose of such a sensor is to obtain a measure of blood oxygen saturation, it also detects changes in blood volume in the skin, and thereby performs PPG sensing. By detecting changes in blood volume, a cyclic signal corresponding to the pulse is obtained. PPG sensors, such as pulse oximeters, are thus commonly used to provide a measure of the pulse rate.

A PPG sensor contains at least one light source (or emitter) such as LED, and one light sensor. The light source (LED) and sensor are placed such that the source (LED) directs light into the skin of the user, which is reflected or transmitted, and detected by the sensor. The amount of reflected/transmitted light is determined by, amongst others, the perfusion of blood within the skin.

The PPG system for example includes a source of red light (red LED), a near-infrared light source (near-infrared LED), and a photodetector diode. The sensor is typically configured with the LEDs and photodetector diode directly on the skin of the patient, typically on a digit (finger or toe) or earlobe.

Other places on the patient may also be suitable, including the forehead, the nose or other parts of the face, the wrist, the chest, the nasal septum, the alar wings, the ear canal, and/or the inside of the mouth, such as the cheek or the tongue.

The light source (LEDs) emit light at different wavelengths, which light is diffused through the vascular bed of the patient's skin and received by the photodetector diode. The changing absorbance at each of the wavelengths is measured, allowing the sensor to determine the absorbance due to the pulsing arterial blood alone, excluding venous blood, skin, bone, muscle, and fat for example. The resulting PPG signal may then be analyzed.

The agreement between PPV and PAV (as measured by PPG) has been found to be poor when compared continuously during surgery. Post-processing may be used to improve the relationship between PPV and PAV, but this may lead to considerable latency.

The PAV derived from the PPG signal is susceptible to more factors in comparison to the PPV derived from the ABP signal. This is because of the presence of vasomotor tone artefact and other measurement noise. Furthermore, the information contained in the PPG signal that can be used for PPV estimation is not fully exploited.

There is therefore a need for an improved signal processing approach, with shorter latency, and able to improve the agreement and correlation between PPV and PAV compared with known methods.

SUMMARY OF THE INVENTION

The invention is defined by the claims.

Examples in accordance with a first aspect of the invention provide a sensor system, comprising: a PPG sensor; and a controller for processing output signals from the PPG sensor, the controller being adapted to generate a modified pulse amplitude variation value based on deriving a baseline variation of the PPG sensor output signal;

deriving a pulse amplitude variation value from the PPG sensor output signal, and performing a pre- or post-adjustment step by which modification is realized in the derived pulse amplitude variation value based on said baseline variation of the PPG sensor output signal, the step comprising:

applying baseline variation compensation to the PPG sensor output signal in advance of deriving the pulse amplitude variation value, based on the derived baseline variation value, and/or subsequent to deriving the pulse amplitude variation value, combining the derived baseline variation value with the derived pulse amplitude variation value to thereby generate the modified pulse amplitude variation value.

The invention is based on insights of the inventors concerning the utility of PPG baseline variation information in improving the agreement and correlation between measured pulse amplitude variation (PAV) and pulse pressure variation (PPV).

In particular, it has been found, contrary to expectations, that combining a baseline variation of a measured PPG signal (e.g. linearly) with a PAV value derived from the PPG signal, leads to improvement in the agreement between the PAV and the equivalent PPV.

Additionally, it has been found that applying baseline compensation to the (raw) measured PPG signal in advance of deriving PAV also leads to improved agreement of the PAV to PPV.

A combination of both approaches, i.e. baseline compensating the PPG signal before determining PAV, and then combining a baseline variation value of the PPG signal with the derived PAV, leads to combined improvements in PAV to PPV agreement.

Thus embodiments of the invention are based on one of two related approaches. A first approach comprises applying baseline variation compensation to the PPG sensor output signal in advance of deriving the pulse amplitude variation value, the derived pulse amplitude variation value then providing (being) the modified pulse amplitude variation value. A second approach comprises first deriving a pulse amplitude variation value from the PPG sensor output signal and subsequently combining this derived baseline variation value with the derived pulse amplitude variation value to thereby generate the modified pulse amplitude variation value.

Baseline variation compensation means compensating the PPG sensor output signal for variation in the baseline of the PPG sensor signal. This may mean adjusting the PPG sensor output signal for variation in the PPG baseline, based on the derived baseline variation, for example processing the signal to compensate for the derived baseline variation. Compensating for the derived baseline variation may comprise adjusting amplitude values of the PPG sensor output signal based on the derived baseline variation value. The compensating may comprise processing the PPG sensor output signal to remove or extract the baseline variation from at least parts of the PPG sensor output signal.

In some examples, baseline variation compensation may in addition comprise performing high pass filtering of the PPG sensor output signal to further filter out the baseline variation from the signal.

Although a pulse amplitude variation value is referred to above, this includes deriving a pulse amplitude variation signal, i.e. a variation in pulse amplitude over time. The baseline variation may be derived based on a variation in PPG pulse maxima (i.e. pulse peak) values over time. Pulse maxima (or pulse peak) values preferably means the absolute values of the pulse peaks or maxima.

A baseline variation calculated by this definition has been found to be much more accurate than other methods, leading to a much better accordance between PAV and PPV when the PAV is modified according to this measure of baseline variation. This time-domain approach is more accurate for example than approaches which derive baseline variation from frequency analysis. This will be explained further below.

According to the above example, the derived baseline variation may be divided by mean PPG pulse amplitude over the time period for which the variation in maxima is calculated. This result in particular has been found to give a very good measure of baseline variation of the PPG signal.

The controller may generally be adapted to derive a series of pulse amplitude variation values or a series of baseline variation values, derived for instance at successive points in time, for instance one for each ventilation cycle in examples. Hence, for the purposes of the following description, steps or processes described in terms of a single value may be understood as applicable equally to a series of values, or an array of values or to a signal representative of a series of values for instance.

Linear combination of a series of values may simply comprise adding each value in the series to each corresponding value in the added series, i.e. in the manner of adding two arrays or matrices of values together.

For the avoidance of doubt, by 'baseline' may be meant the middle or center or base level or median level of a signal, i.e. the level about which a signal oscillates or pulses. 'Baseline' is well recognized term in the art and its standard meaning is to be applied for the purposes of this disclosure.

By baseline variation is meant the change in this baseline level of the PPG signal, for instance the change over time. Compensating for baseline variation may comprise deriving a baseline variation as a function of time, for instance a baseline variation signal, and linearly combining this with for instance a derived pulse amplitude variation signal.

In examples, the PPG sensor may be a finger or forehead PPG sensor. By this is meant that the sensor may be a sensor for measuring PPG at the finger or at the forehead.

Sensors for other parts of the body may also be used. Finger sensors are the most common form of PPG sensor for extended monitoring of patients and are highly convenient. It is generally speculated that forehead-derived PAV may be more robust that finger-derived PAV. However, it may also be more vulnerable to noise.

In accordance with at least one set of embodiments, the sensor system may make use of readings from two PPG sensors.

In particular, in accordance with one or more embodiments, the system may further comprise: a second PPG sensor; and wherein the controller is for processing output signals from the PPG sensor and the second PPG sensor, the controller being further adapted to:

derive a second modified pulse amplitude variation value based on deriving a pulse amplitude variation value from the second PPG sensor output signal and performing said adjustment step in respect of the second derived pulse amplitude variation value based on a baseline variation of the second PPG sensor output signal to thereby realize an adjustment in the second pulse amplitude variation value, and derive an output pulse amplitude variation signal based on a combination of the modified pulse amplitude variation values for the PPG sensor and the second PPG sensor.

In accordance with this set of embodiments, an output pulse amplitude variation (PAV) is derived based on a combination of PAV values derived from PPG readings of each of two PPG sensors.

Preferably, the PPG sensors are configured to relate signals corresponding to different regions of the body.

In advantageous examples, one of the PPG sensors may be a finger PPG sensor and the other may be a forehead PPG sensor.

As noted above, it is generally understood that forehead-derived PAV may be more robust that finger-derived PAV. This is suggested to arise from the fact that forehead PPG, measured at the cephalic region, may offer more insight into the central circulation. However, the measurement of forehead PPG may suffer from low AC:DC ratio, rendering it potentially more vulnerable to noise than finger derived PPG.

However, combining PPG signals from the finger and forehead leads to improvements in agreement and correlation between the output PAV and PPV.

In particular examples, the controller may be adapted to derive an output pulse amplitude variation as the mean of the modified pulse amplitude variation values for the PPG sensor and the second PPG sensor.

In alternative examples, the controller may be adapted to derive an output pulse amplitude variation as a different type of average of the modified pulse amplitude variation values for the PPG sensor and the second PPG sensor, or for instance a linear combination of the values for the PPG sensor and second PPG sensor.

The baseline variation compensation applied to the PPG signal may take different forms.

In accordance with one or more examples, the baseline variation compensation may comprise performing high-pass filtering. This is a very simple and fast approach to removing the effect of baseline variation from the PPG signal. However, in some cases this may be less than fully accurate or complete in compensating for baseline variation effects. In particular, in certain circumstances, baseline variation can itself exhibit fast alterations, thereby also having high-frequency components.

In accordance with further examples, the baseline variation compensation may comprise for the each PPG sensor, deriving a baseline variation of the PPG sensor output signal and processing the PPG sensor output signal to compensate for the derived baseline variation.

Compensating may comprise for instance adjusting values of the PPG sensor output signal. The compensating may comprise adjusting amplitude values of the PPG sensor output signal. The compensating may comprise processing the PPG sensor output signal to remove or extract the baseline variation from at least parts of the PPG sensor output signal. For the purpose of combining the baseline variation with the derived PAV, in accordance with one or more examples, deriving a baseline variation value from the PPG sensor output signal may be based on deriving a variation in pulse maximum value or variation in pulse mean value over time of the PPG.

By pulse maximum value is meant the value of the signal at peaks in pulses of the signal. This approach to deriving baseline variation is based on processing in the time domain. Known prior art approaches are based on processing in the frequency domain. By working in the time domain, baseline variation may be extracted based on a pulse-wise analysis: examining variation in baseline on a pulse-wise level, rather than in frequency domain in which baselines of multiple pulses are necessarily analyzed together.

Advantageously, the variation in pulse maximum value may be divided by an average pulse amplitude for the time period considered, to thereby derive a measure of baseline variation value.

In examples, the adjustment step may comprise both the applying baseline variation compensation and the combining a baseline variation of the PPG sensor output signal with the derived pulse amplitude variation value. As noted above, a combination of both of these approaches achieves combined improvements in agreement between derived PAV and underlying PPV.

In examples, the combining the derived baseline variation value of the adjustment step may comprise performing a linear combination of the derived baseline variation value with the derived pulse amplitude variation value. By linear combination is meant a linear sum, i.e. linear combination=$\alpha$[derived baseline variation value]+$\gamma$[pulse amplitude variation value], where $\alpha$ and $\gamma$ are linear coefficients.

In examples, the linear coefficient for the baseline variation (i.e. $\alpha$) may be greater than the linear coefficient for the pulse amplitude variation (i.e. $\gamma$). This is because the coefficient of the PAV component by itself does not directly quantify the full contribution of PAV, since the BV amplifies the PAV contribution when linearly combined. For this reason, it is preferable that the PAV coefficient is lower than that of the BV linear combination.

As noted above, generally, the controller may be adapted to derive a series of PAV values and/or a series of BV values, relating to different time points, for instance each value acquired for each ventilation cycle.

In accordance with any example, the controller may be adapted for the or each PPG sensor to apply a median filter to the pulse amplitude variation (PAV) values and/or the baseline variation values from the PPG sensor output signal. In examples, in embodiments in which the baseline variation of the PPG sensor signal is combined with the PAV signal for said adjustment step, both the PAV and the baseline variation value series' may be applied with a median filter.

In accordance with one or more examples, a median filter may be applied to derived modified PAV values. In particular, in the case that the adjustment step comprises applying baseline variation compensation to the PPG sensor output signal, the controller may be adapted to apply a median filter to the modified PAV value thereby derived.

Application of a median filter assists in removing noise from the baseline variation signal or value and/or from the pulse amplitude variation signal or value.

Examples in accordance with a further aspect of the invention provide a method of deriving a modified pulse amplitude variation, comprising:
measuring a PPG signal;
deriving a baseline variation of the PPG signal; and
deriving a pulse amplitude variation from the PPG signal;
wherein the method further includes performing a pre- or post-adjustment step by which a modification is realized in the derived pulse amplitude variation based on the baseline variation of the PPG signal, the step comprising:
applying baseline variation compensation to the PPG signal in advance of deriving the pulse amplitude variation value, based on the derived baseline variation; and/or
subsequent to deriving the pulse amplitude variation, combining the derived baseline variation with the derived pulse amplitude variation to thereby generate the modified pulse amplitude variation.

In accordance with at least one set of embodiments, the method may further comprise: measuring a second PPG signal: deriving a second modified pulse amplitude variation by:
deriving a second pulse amplitude variation from the second PPG signal, and performing a pre- or post-adjustment step by which modification is realized in the second derived pulse amplitude variation based on a derived baseline variation of the second PPG signal, the step comprising:
applying baseline variation compensation to the second PPG signal in advance of deriving the second pulse amplitude variation, based on the derived baseline variation; and/or
subsequent to deriving the pulse amplitude variation, combining the derived baseline variation of the second PPG signal with the second derived pulse amplitude variation to thereby generate the second modified pulse amplitude variation; and
deriving an output baseline variation signal based on a combination of the modified pulse amplitude variations for the PPG sensor and the second PPG sensor.

In accordance with one or more embodiments, the baseline variation compensation may comprise for the or each PPG signal, deriving a baseline variation of the PPG signal and processing the PPG signal to compensate for the derived baseline variation.

Examples in accordance with a further aspect of the invention provide a computer program product comprising computer program code means which is adapted, when run on a computer, to perform any of the methods described above or defined in any claim of the present application.

BRIEF DESCRIPTION OF THE DRAWINGS

Embodiments of the invention will be described, by way of example only, with reference to the drawings, in which.

DETAILED DESCRIPTION OF THE EMBODIMENTS

The invention provides a sensor system in which output signals of at least one PPG sensor are processed to derive a modified pulse amplitude variation (PAV) value, being modified to take account of a baseline variation of the PPG sensor output signal. In particular, the modified PAV is derived through performing a modification step in which either: a baseline variation of the PPG sensor output is derived and combined with a previously derived PAV, or, a PPG sensor output is first processed to perform baseline variation compensation, in advance of then deriving a PAV from the compensated signal.

Either approach has been shown to improve agreement and correlation between the derived PAV (the modified PAV) and pulse pressure variation (PPV) for which PAV in many scenarios acts as a non-invasive surrogate.

Figure 1:
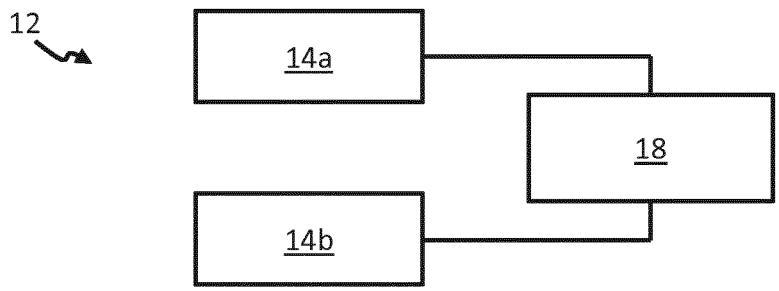
FIG. 1 shows an example system in accordance with one or more embodiments.

The basic architecture of an example sensor system 12 in accordance with one or more embodiments of the present invention is shown in block diagram form in FIG. 1.

The sensor system 12 comprises a controller 18 being operatively coupled with two photoplethysmogram (PPG) sensors 14a, 14b.

In use, the two PPG sensors 14a, 14b are advantageously applied to different parts of the body, for deriving PPG readings at different anatomical locations. The PGG sensors in advantageous examples may in use be applied to a patient's finger and forehead. In examples, the two sensors may be designed for use at different parts of the body. Advantageously, the sensors are a finger PPG sensor 14a and a forehead PPG sensor 14b.

The system may further comprise a display (not shown), the controller 18 being adapted to control the display to show results of the modified PAV calculation. The controller may be adapted to control the display to show results in real time.

Although two PPG sensors are provided in the example of FIG. 1, as will be explained below, alternative embodiments may comprise just one PPG sensor.

The controller is adapted to process output signals of the PPG sensors to derive from each of them modified pulse amplitude variation (PAV) signals. PAV signals or values are standardly derived from a PPG sensor signal by determining exhibited variation in the signal amplitude or power of a raw PPG sensor output and either expressing this as a single figure or monitoring its change over time.

In accordance with the invention an adjustment step is performed to factor in baseline variation information concerning the PPG signal. Baseline modulation or variation has been associated with volume status. The baseline variation of the PPG therefore in effect contains or embodies additional physiological information which if utilized in an appropriate way when deriving a measure of PAV can provide a more accurate measure of underlying pulse pressure variation (PPV) for which PAV is a surrogate.

The inventors have found that the PPG baseline variation information should be incorporated into the PAV determination calculation in different ways depending upon the stage at which it is introduced.

Where baseline variation information is to be factored in in advance of initially deriving a PAV value from the PPG signal, best results are achieved if the baseline variation (BV) information is 'subtractively' incorporated, i.e. a baseline variation is extracted or filtered from the raw PPG sensor signal, or where the PPG sensor signal is otherwise processed to compensate for the baseline variation it exhibits.

Where the PPG baseline variation information is to be factored in after initial derivation of a PAV value from the PPG signal, best results are achieved if it is 'additively' incorporated, i.e. where the PAV is combined with a derived baseline variation of the PPG.

Greatest improvements in agreement or correlation between PAV and PPV are achieved where both approaches are applied together, i.e. where the PPG signal is processed to compensate for the baseline variation or to remove/filter the baseline variation, and then subsequently the result of the compensation or filtering is then combined with the baseline variation of the original raw PPG signal to derive a modified PAV.

Where two sensors are used, the modified PAV derived from the two may be averaged in examples to further improve agreement with PPV.

The notion that 'additive' and 'subtractive' incorporation of PPG baseline variation information may both be beneficial to the agreement of PAV with PPV, if applied at different stages in the processing, is counterintuitive and has not been previously suggested or considered in the field.

These various general approaches to processing the PPG signal output(s) will now be described in detail with reference to FIGS. 1-6, which illustrate process steps performed by the controller in a set of example system embodiments.

For ease of reference, a list of reference numerals pertaining to the processing approaches depicted in FIGS. 2-6 are provided at the end of this disclosure. Similar individual steps are indicated by like reference numerals. Similar outcome or result stages are also indicated by like reference numerals, regardless of the particular process by which they were arrived at. In particular, all instances of a modified PAV are indicated by the same reference numeral, despite being arrived at by different particular processes or combinations of steps in different cases.

It is noted that a controller of a single system may in examples be adapted to perform more than one of the outlined approaches. A controller 18 may for instance have a plurality of operating modes, in accordance with each of which the controller is adapted to perform a different one of the outlined processing approaches.

Figure 2:
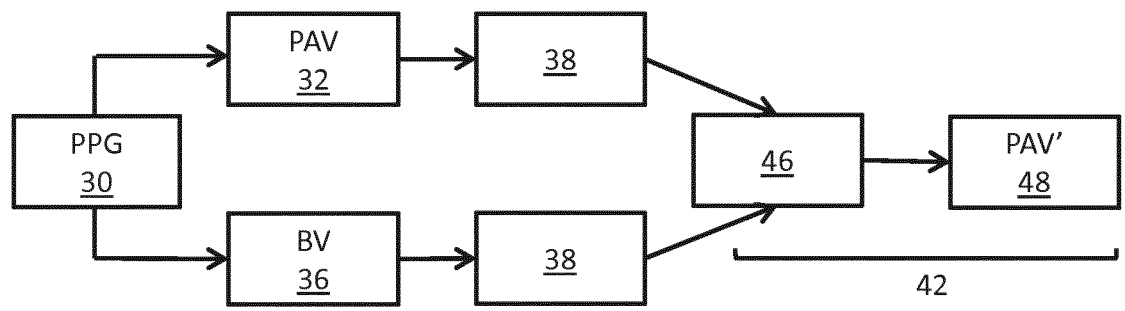
FIG. 2 shows a first processing approach which may be applied by a controller in accordance with one or more embodiments to derive a modified pulse amplitude variation value.

FIG. 2 shows a first processing approach in accordance with one or more embodiments of the invention.

In accordance with the first approach, a PPG sensor output signal 30 is processed to derive a pulse amplitude variation (PAV) 32 from the PPG signal. The PAV may be derived using standard procedures known in the art for deriving a PAV from a PPG signal.

The PPG sensor output signal 30 is also processed to derive a baseline variation (BV) 36 of the PPG sensor signal.

A baseline variation can be derived from a PPG sensor output signal using frequency-domain analysis. In particular, it is known to derive baseline modulation of a PPG signal by determining a ratio between power at the ventilation frequency and power at the cardiac frequency (Shelley K H, Jablonka D H, Awad A a., Stout R G, Rezkanna H, Silverman D G. What is the best site for measuring the effect of ventilation on the pulse oximeter waveform? *Anesth Analg.* 2006: 103 (2): 372-377).

However, this measure can be inaccurate. In particular, the physiological signals are often non-stationary during surgery, causing a violation of one of the assumptions of the Fourier Transform used to perform the frequency analysis.

To address this, inventors of the present invention propose in accordance with preferred embodiments of the invention to utilize a different measure of baseline modulation, termed 'baseline variation' (BV). This measure of baseline variation is derived in the time domain instead of the frequency domain, avoiding the assumption errors which arise when frequency based analysis is used. This approach is not known in the art.

In particular, a baseline variation is derived based on a determination of variation in PPG pulse maxima (or pulse peak value) over time. Baseline variation calculated in this way has been found to provide a much more accurate measure of baseline variation, leading to improved accordance between the modified PAV and the PPV.

The derived variation may be divided by mean pulse amplitude over the time period for which the variation in maxima is calculated. This result in particular has been found to give a very good measure of baseline variation of the PPG signal.

Both the derived PAV 32 and derived BV 36 are separately processed with a median filter 38 to remove noise. In certain advantageous examples, the length of the filter may be set to a value between 3 and 7. A value of between 3 and 7 represents an advantageous trade-off between latency incurred by the filter and the beneficial smoothing effect of the filter. Too long a filter may lead to an unacceptable delay in processing incurred by the filter. A particularly advantageous value for the filter length in respect of this trade-off is five.

Other lengths, outside of the given range, may also be used. The step of applying the median filter is optional and may be omitted.

Following application of the median filter 38, an adjustment step 42 is performed by which the BV information is introduced or incorporated into the PAV measurement.

In the first example approach of FIG. 2, the PAV 32 and BV 36 are combined. In particular, the two values or signals may be additively combined. In preferred examples, a linear combination 46 is performed of the two signals. This linear combination thereby derives a modified pulse amplitude variation 48 (labelled PAV' in FIG. 2) which incorporates baseline variation information.

By linear combination is meant that linear multiples of the PAV and BV are added together to derive the modified PAV, i.e.

Modified PAV=Linear Combination=α[PAV]+γ[BV]

where α and γ are linear coefficients.

In advantageous examples, the coefficients for PAV and BV may be between 0.50 and 0.60 and between 0.90 and 1.00 respectively where a finger PPG is used. In cases where a forehead PPG is used, the coefficients for the PAV and BV may in advantageous examples be between 0.20 and 0.30 and between 5.00 and 5.20 respectively. In more particular examples, for a finger PPG, coefficients for the PAV and BV may be 0.53 and 0.94 respectively, and for a forehead PPG, may be 0.22 and 5.10 respectively.

These values have been derived empirically by the inventors as values which achieve particularly beneficial results in terms of improving agreement between PAV and PPV when used as linear coefficients in the linear combination.

As noted above, baseline variation has been known to be associated with volume status. By taking a linear combination of PAV and BV, additional information regarding volume status is assimilated with the standard PAV measurement. At the same time, noise from the PAV is suppressed by the introduction of an additional parameter.

The approach of FIG. 2 has been tested for each of finger and forehead derived PAV, to determine the degree of agreement with PPV (of which PAV provides a proxy measure), and the improvement compared with standard PAV measurement. The results are presented in Tables 1 and 2 below. Table 1 lists various measures of agreement between standardly derived PAV and PPV and Table 2 shows the corresponding results for the new Modified PAV, derived using the linear combination approach outlined above and presented in FIG. 2.

TABLE 1

Agreement between Standard PAV and PPV

|  | Finger | Forehead |
|---|---|---|
| Mean ± $SD^a$ of difference between PAV and PPV | 3.2% ± 5.1% | 12.0% ± 9.1% |
| Correlation coefficients | 0.70 | 0.60 |
| Concordance rate | 84% | 83% |

$^a$SD: standard deviation

TABLE 2

Agreement between Modified PAV and PPV

|  | Finger | Forehead |
|---|---|---|
| Mean ± $SD^a$ of difference Between PAV and PPV | −0.7% ± 3.0% | −0.43% ± 3.2% |
| Correlation coefficients | 0.70 | 0.61 |
| Concordance rate | 89% | 88% |

$^a$SD: standard deviation

It is noted that the first row in each of Table 1 and Table 2 shows the mean and standard deviation of the difference between the derived pulse amplitude variation (PAV) (or modified PAV) and corresponding pulse pressure variation. The smaller the (modulus of the) shown percentage, the greater the degree of average correspondence between each derived PAV measurement and each corresponding PPV measurement.

It can be seen that for both finger and forehead PPG sensors, there is achieved for the modified PAV a marked decrease in the mean difference between PAV values and corresponding PPV values. There is also in both cases a clear increase in the concordance rate between the derived PAV and PPV (for the modified PPV). By concordance rate is meant a measure of the trending relationship between PAV and PPV, i.e. how closely PAV is able to follow the trend of PPV. By correlation coefficient is mean the Pearson correlation coefficient.

Figure 3:
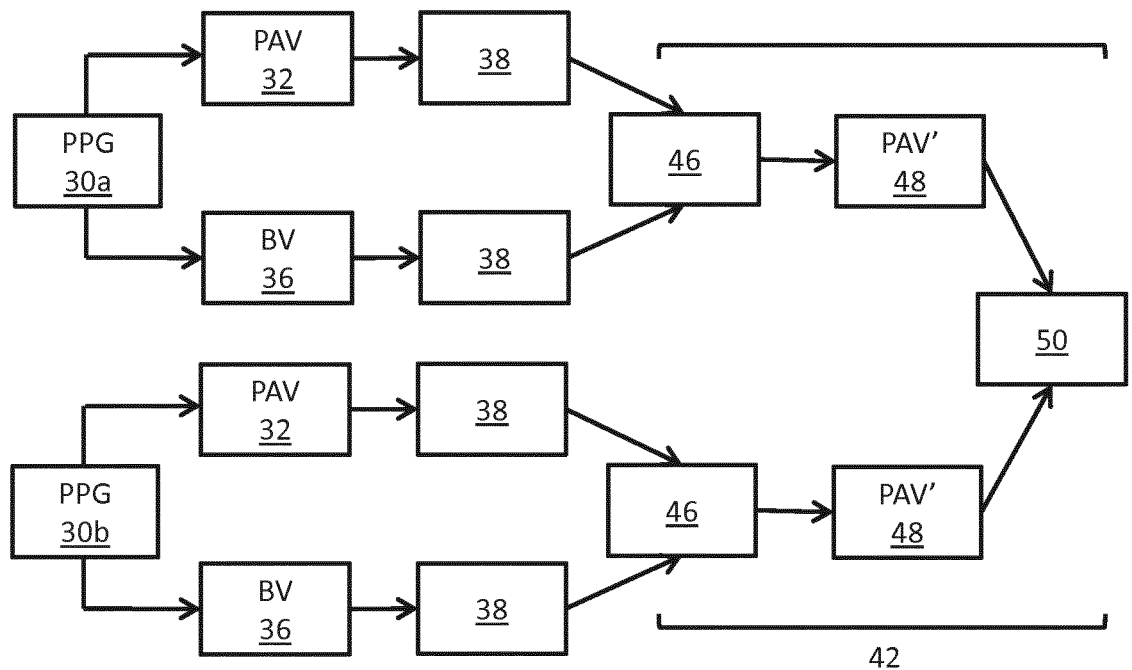
FIG. 3 shows a second processing approach which may be applied by a controller in accordance with one or more embodiments.

FIG. 3 shows a second processing approach as may be implemented in examples of the present invention to derive a modified pulse amplitude variation (PAV).

This second approach is based on combining results obtained from PPG sensor output signals derived from two different PPG sensors, being located at different parts of the body. This has been found to improve results.

In particular, the approach of FIG. 3 comprises performing the first processing approach shown in FIG. 2 and described above (comprising linearly combining baseline variation (BV) 36 and pulse amplitude variation 32 to derive a modified PAV 48 (labelled PAV')) separately for first and second output signals 30a, 30b of each of two PPG sensors, and then deriving the mean 50 of the two derived modified PAV results. The mean then provides a final output PAV.

In this case, the steps of deriving the linear combination 46 for each of the first output signal 30a and second output signal 30b, and then deriving the mean of the resulting modified PAV values constitute the adjustment step 42 of the processing approach.

In particularly advantageous examples, the two PPG sensor signals may be signals from a finger and forehead PPG sensor respectively. It is generally understood in the field that forehead-derived PAV values may be more robust and reliable than equivalent finger-derived PAV.

This understanding originates from the fact that forehead PPG, measured at the cephalic region, is understood to provide a better measure of central circulation. However, forehead PPG measurement typically experiences low AC/DC ratio, rendering it vulnerable to noise.

However, a combination of finger and forehead derived PPG has been found to improve agreement and correlation between PAV and PPV, even further than the processing of FIG. 2 applied alone. Thus, the approach of FIG. 3 in advantageous examples comprises applying the processing method of FIG. 2 to PPG signals derived from each of a finger and forehead PPG and subsequently taking the mean of the respectively derived results.

This approach has been tested for finger and forehead derived PAV, and the degree of agreement with PPV (of which PAV is a proxy measure), identified. The results are presented in Table 3. These may be compared with the results of Table 1 and 2 above.

TABLE 3

Agreement between mean of modified PAV and PPV

|  | Mean of Finger and Forehead Modified PAV |
|---|---|
| Mean ± $SD^a$ of difference between PAV and PPV | −0.6% ± 2.4% |
| Correlation coefficients | 0.80 |
| Concordance rate | 92% |

It can be seen that the (modulus of the) mean difference between modified PAV values and equivalent PPV values is slightly lower where the mean is taken of finger and forehead derived values than where only the PPG for finger is considered (see Table 2).

Furthermore, by taking the average, the correlation coefficient is significantly improved compared with achieved values for finger and forehead PAV considered separately, and the concordance rate is also improved.

Figure 4:
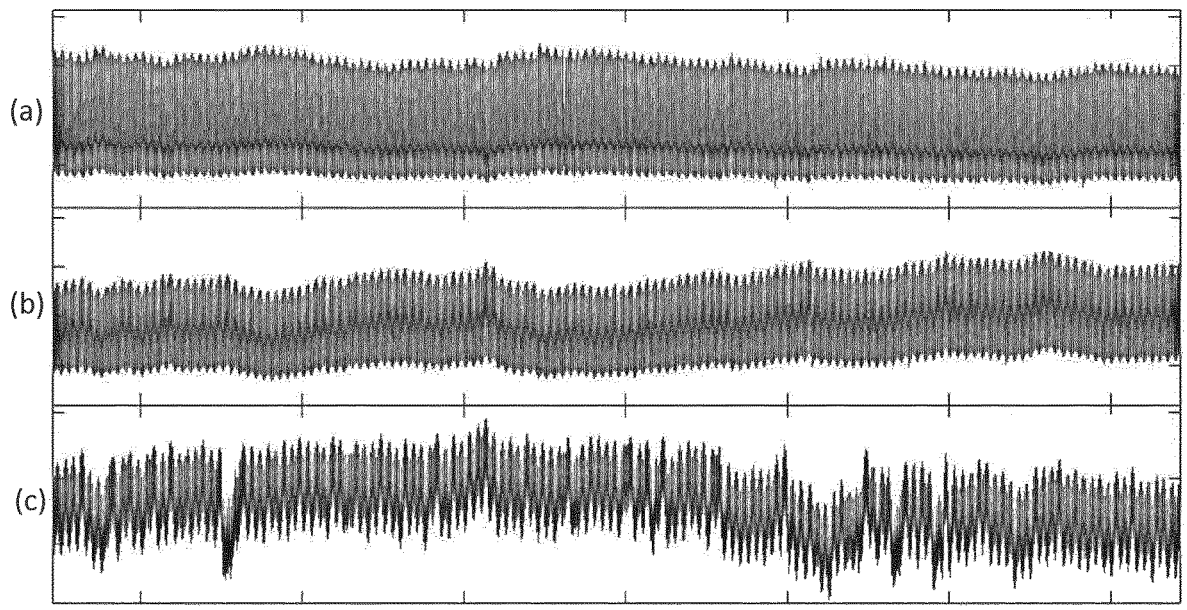
FIG. 4 shows example waveforms for pulse pressure variation, and for PPG amplitude signals over time.
Figure 5:
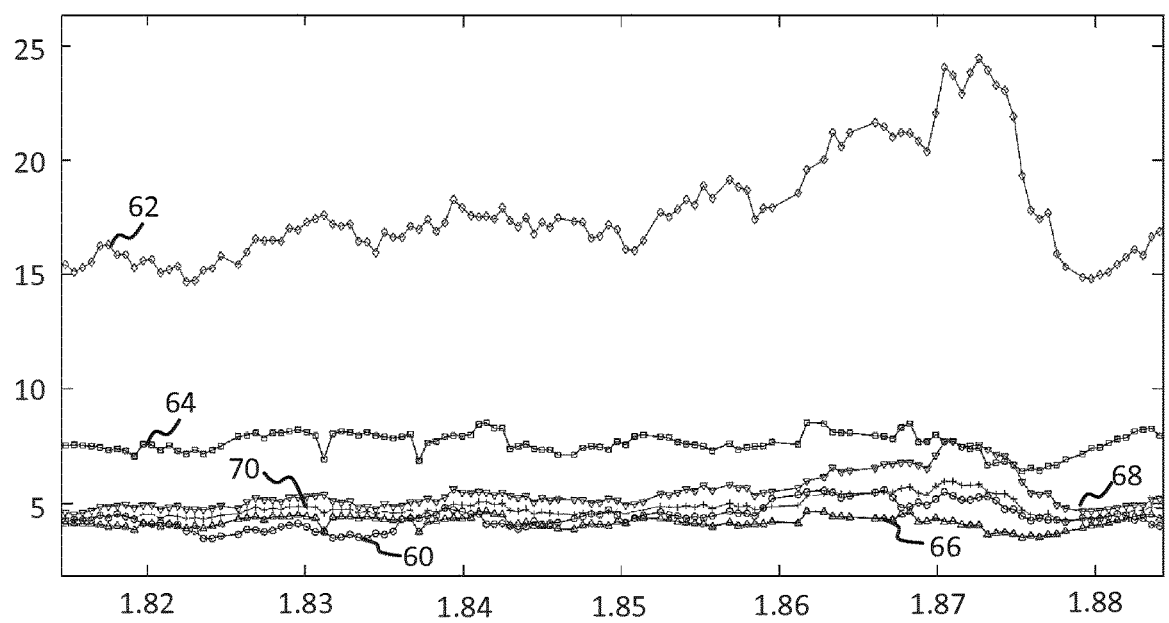
FIG. 5 illustrates results of derived modified PAV values compared with standard methods.

The results presented in Tables 1-3 are illustrated graphically in FIGS. 4 and 5.

FIG. 4 shows for illustration sample waveforms for, in (a), an (invasive) arterial blood pressure (ABP) signal, in (b), PPG signal for a finger PPG sensor, and in (c), PPG signal for a forehead PPG sensor.

Waveform (a) shows ABP in the form of pressure (y axis: mmHg, i.e. 133.322 Pascals) vs time (x, axis: seconds). Waveform (b) shows a PPG sensor output signal for a finger sensor, in the form of PPG sensor signal (y-axis: nA/mA) vs time (x-axis: seconds). Waveform (c) shows a PPG sensor output signal for a forehead sensor, in the form of sensor signal (y-axis: nA/mA) vs time (x-axis: seconds).

The unit nA/mA is a common unit used for expressing PPG sensor signal. It represents the photo current in the photodiode (the sensor) of the PPG sensor (units nano Ampere) divided by the LED current (units milliAmpere).

As discussed above, a PPG sensor contains at least one LED, and one light sensor. The LED and sensor are placed such that the LED directs light into the skin of the user, which is reflected or transmitted, and detected by the sensor. The amount of reflected/transmitted light is determined by, amongst others, the perfusion of blood within the skin.

Hence nA/mA represents the current in the light sensor (photodiode) in units of nA divided by the current in the LED in units of mA.

The variation in the amplitude of the PPG signals (b) and (c) (that is, the variation in the amplitude of pulses in the PPG signals (b) and (c)) over time gives pulse amplitude variation (PAV).

The results presented in Tables 2 and 3 are illustrated in FIG. 5, in graphical form. The y-axis represents the signal values for each of the results. The x-axis represents time, in seconds.

In particular, line 60 shows the result for (invasive) arterial blood pressure (ABP) measured PPV. Line 62 shows the result for standard PAV derived from a forehead PPG sensor output. Line 64 shows the result for standard PAV derived from a finger PPG sensor output. Line 66 shows the modified PAV derived using the method of FIG. 2, as derived from a finger PPG. Line 68 shows the modified PAV derived using the method of FIG. 2, as derived from a forehead PPG. Line 70 shows the modified PAV derived using the method of FIG. 3 in which modified PAV values derived from each of a finger and forehead PPG sensor outputs are averaged (mean is taken) to derive a final modified PAV output.

Hence all signal results are presented together on a common set of axes, with y-axis representing each signal's value at a given time, and x-axis representing time.

The results as shown in FIG. 5 illustrate the results of Table 1. In particular, it can be seen the large difference between standard forehead-derived PAV 62 compared to the PPV signal 60. The difference between standard finger-derived PAV 64 and the PPV signal 60 is also relatively large.

On the contrary, it can be seen the very close agreement between the PPV signal and each of the modified PAV derived from a finger PPG 66, the modified PAV derived from a forehead PPG 68, and the modified PAV 70 consisting of the mean of signals 66 and 68.

Figure 6:
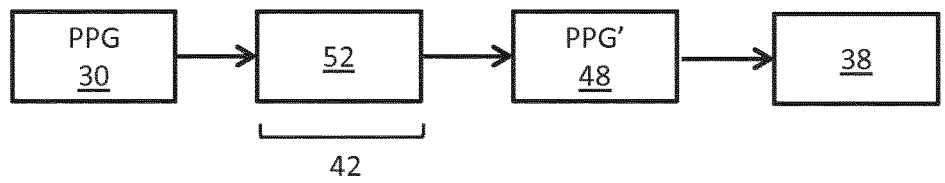
FIG. 6 illustrates a further processing approach as may be applied by a controller in accordance with one or more embodiments.

FIG. 6 shows a third processing approach for deriving a modified PAV. This third approach is based on taking account of the PPG sensor output signal baseline variation before determination of the PAV value. This is based on the finding of the inventors that the presence of strong baseline variation can influence the accuracy of the initial computation of PAV. While combining the PPG baseline variation with the derived PAV improves the agreement with ABP PPV, it cannot remedy the initial influence of the BV in the determining the PAV.

Hence in accordance with the third approach, the PPG sensor output signal 30 is first processed to apply baseline variation compensation 52, before a PAV is then derived.

In accordance with one set of examples, the compensating 52 comprises extracting the baseline variation from the PPG sensor output by applying to the PPG sensor output signal 30 a high-pass filter. The high pass filter acts to retain the relatively fast varying PPG signal part, whilst removing the relatively slow varying baseline variation part. This hence suppresses the baseline variation in the PPG sensor output before computing PAV.

After application of the high pass filter, a PAV is then derived from the filtered PPG, the PAV being a modified PAV 48 (labelled PAV'), modified as a consequence of the pre-extraction of the baseline variation from the PPG sensor signal.

Optionally, the thus derived modified PAV 48 is then processed with a median filter 38 to remove noise.

In certain advantageous examples, the cut-off frequency for the high pass filtering may set at be 0.4 Hz. Baseline variation in PPG signals can typically be expected to fall below this frequency.

In accordance with this processing approach, the adjustment step 42 by which baseline variation information is introduced into the derived PAV comprises just the baseline variation compensation 52, performed in advance of calculation of the PAV.

In accordance with a further set of examples, the baseline variation compensation 52 comprises processing pulses of the PPG sensor output signal in the time domain in order to adjust the PPG sensor signal pulses to compensate for the baseline variation.

Figure 7:
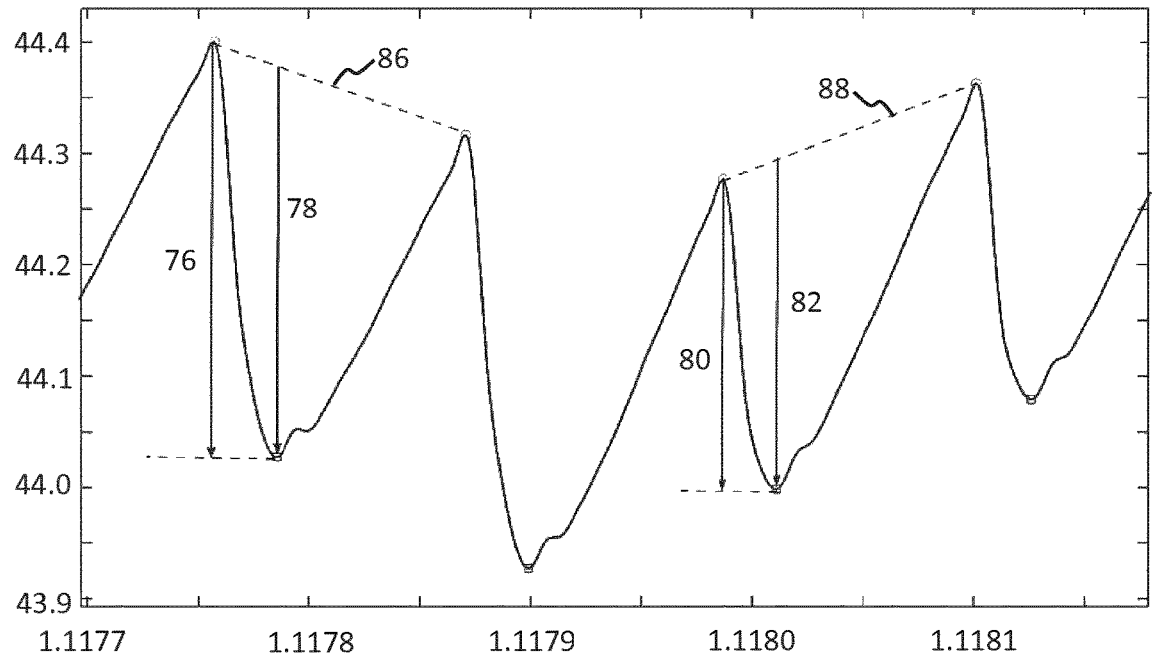
FIG. 7 illustrates baseline variation compensation applied to a PPG sensor output signal.

This compensation approach is illustrated in FIG. 7, which shows a portion of an example PPG sensor output signal. Lines 76, 80 show PPG signal amplitudes at two points before compensation, and lines 78, 82 show the same respective PPG signal amplitudes after compensation. Inclined lines 86, 80 illustrate the slope in the baseline of the signal PPG between consecutive peaks. It can be seen that this variation in the baseline leads to an error in determination of the amplitude without, in the absence of any applied compensation. The compensated pulse amplitude 78, 82 take account of the variation in the baseline, in particular by modifying the PPG sensor signal.

The pulse compensation approach in more detail comprises the following steps. First, the peaks in the PPG signal are identified. The PPG signal is then compensated by transforming each pulse segment (where one pulse segment is the portion of the PPG signal in-between two consecutive peaks) such that the second peak of each pulse segment is shifted to the same height (level) as the first peak of the pulse segment, while linearly transforming the intermediate signal accordingly, e.g. transforming the intermediate signal such that it follows the same general shape or trend as the previous signal, but adjusted so that the baseline of that signal is level, i.e. so that the intermediate signal portion leads to the shifted-height second peak.

Following this, all subsequent pulse segments are brought to the same height (level) such that the compensated signal will have all its peaks at exactly the same height (level), with the intermediate signal transformed accordingly. The final level to which these peaks are adjusted can be chosen arbitrarily, as this height in itself does not directly affect the final derived PAV signal (which is based on variations in amplitude only, independent of the actual signal level).

This compensation approach leads to a more accurate final derived PAV. This is because the baseline variations in the PPG signal greatly amplify the derived PAV in a non-linear way: the amplification effect on the derived PAV is greater than simply the proportionate increase in BV. For this reason, there is no simple linear relationship between the non-corrected PAV and the true PPV by which correction might easily be performed. The method presented above solves this issue in a numerically stable way.

In accordance with a fourth processing approach, the approach of FIG. 6 is applied separately to PPG sensor output signals of two PPG sensors. Preferably, these are signals attached to different parts of the body. Preferably, the two sensors are a finger PPG sensor and a forehead PPG sensor.

The processing of FIG. 6 is applied to the signal output of each, and the modified PAV 48 results for each then averaged (the mean taken) to derive a final modified PAV result. As in the case of the approach of FIG. 3, by taking the mean of modified PAV results of a finger and forehead derived PAV, the agreement of the final result with the equivalent PPV signal is improved. Optionally, as in FIG. 6, a median filter 38 may be applied to the modified PAV results obtained from each of the two PPG sensor outputs before the mean is taken.

Figure 8:
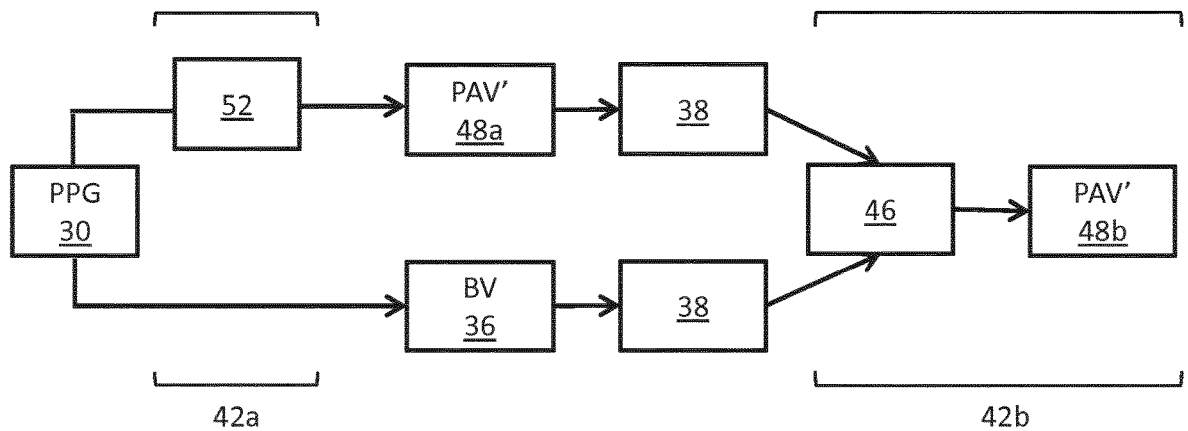
FIG. 8 shows a further processing approach as may be applied by a controller in accordance with one or more embodiments.

FIG. 8 illustrates a fifth processing approach. In accordance with this approach the approaches of FIG. 2 and FIG. 6 are combined, so that both additive and subtractive incorporation of baseline variation information is applied.

In particular, a PPG sensor output signal 30 is processed to apply baseline variation compensation 52, as in FIG. 6. The baseline variation compensation may in examples comprise application of a high pass filter or application of pulse compensation, as illustrated in FIG. 7.

A first modified PAV 48a (labelled PAV') is then derived from the pre-processed PPG signal.

Separately, the raw (uncompensated) PPG sensor output signal 30 is processed to derive a baseline variation (BV) 36 of the PPG signal in a manner as discussed above in relation to the method of FIG. 2.

Optionally both the BV 36 and the first modified PAV 48a are processed with a median filter 38 to reduce noise.

The (median filtered) first modified PAV 48a and BV 36 are then linearly combined to provide linear combination 46 to derive a final modified PAV 48b.

This approach makes full use of the baseline variation information contained in the PPG signal, exploiting the improvements derivable both from additive and subtractive incorporation of BV information into the modified PAV determination.

In accordance with this approach, the adjustment step may be understood to comprise two parts: a first part 42a in which baseline variation compensation 52 is applied to the raw PPG sensor output signal 30 and a second part 42b in which the linear combination 46 is performed of the BV 36 and the first modified PAV 48a.

In accordance with a final example processing approach, the approach of FIG. 8 is applied separately to signals derived from output signal of each of two PPG sensors, where preferably these are a finger PPG sensor and a forehead PPG sensor. The final modified PAV 48b for each of the PPG sensors are then combined in the form of a mean to derive an output pulse amplitude variation value being an average of the two. Taking an average of signals derived from two parts of the body, and most advantageously from the finger and forehead has been shown to improve the agreement of the final derived output PAV compared to equivalent PPV readings.

As discussed above, example sensor systems in accordance with the present invention may be of particular utility in determining or monitoring or assessing circulatory volume status via fluid responsiveness. Improved PAV provides a reliable surrogate for PPV which in turn provides an indirect indication of fluid responsiveness. Fluid responsiveness gives an indirect indication of circulatory volume status.

However, the system is of use in any scenario in which non-invasive estimation of PPV is required.

As discussed above, embodiments make use of a controller. The controller can be implemented in numerous ways, with software and/or hardware, to perform the various functions required. A controller is one example of a controller which employs one or more microcontrollers that may be programmed using software (e.g., microcode) to perform the required functions. A controller may however be implemented with or without employing a controller, and also may be implemented as a combination of dedicated hardware to perform some functions and a controller (e.g., one or more programmed microcontrollers and associated circuitry) to perform other functions.

Examples of controller components that may be employed in various embodiments of the present disclosure include, but are not limited to, conventional microcontrollers, application specific integrated circuits (ASICs), and field-programmable gate arrays (FPGAs).

In various implementations, a controller or controller may be associated with one or more storage media such as volatile and non-volatile computer memory such as RAM, PROM, EPROM, and EEPROM. The storage media may be encoded with one or more programs that, when executed on one or more controllers and/or controllers, perform the required functions. Various storage media may be fixed within a controller or controller or may be transportable, such that the one or more programs stored thereon can be loaded into a controller or controller.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single controller or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

LIST OF REFERENCE NUMERALS RELATING TO FIGS. 2-6

30 PPG Sensor output signal
32 Standard pulse amplitude variation
36 Baseline variation of a PPG sensor output signal
38 Median filter
42 Adjustment step 46 Linear combination
48 Modified pulse amplitude variation (labelled PAV')
52 High pass filter.

The invention claimed is:
1. A sensor system, comprising:
a photoplethysmography (PPG) sensor;
a controller configured to process output signals from the PPG sensor, the controller being adapted to generate a modified pulse amplitude variation value based on:
deriving a baseline variation of the PPG sensor output signal;
deriving a pulse amplitude variation value from the PPG sensor output signal; and
performing a post-adjustment step by which modification is realized in the derived pulse amplitude variation value based on said baseline variation of the PPG sensor output signal, wherein the post-adjustment step comprises:
subsequent to deriving the pulse amplitude variation value, combining the derived baseline variation additively with the derived pulse amplitude variation value to thereby generate the modified pulse amplitude variation value.

2. The sensor system as claimed in claim 1, wherein the baseline variation is derived based on a variation in pulse maxima values of the PPG over time.

3. The sensor system as claimed in claim 1, wherein the PPG sensor is one of: a finger PPG sensor or forehead PPG sensor.

4. The sensor system as claimed in claim 1, further comprising:
a second PPG sensor;
wherein the controller is further configured to process output signals from the PPG sensor and the second PPG sensor,
the controller being further adapted to:
generate a second modified pulse amplitude variation value based on deriving a pulse amplitude variation value from the second PPG sensor output signal and performing said post-adjustment step in respect of the second derived pulse amplitude variation value based on a baseline variation of the second PPG sensor output signal to thereby realize a modification in the second pulse amplitude variation value; and
derive an output pulse amplitude variation signal based on a combination of the modified pulse amplitude variation values for the PPG sensor and the second PPG sensor.

5. The sensor system as claimed in claim 4, wherein one of the PPG sensors is a finger PPG sensor and the other is a forehead PPG sensor.

6. The sensor system as claimed in claim 4, wherein the controller is adapted to derive an output pulse amplitude variation as a mean of the modified pulse amplitude variation values for the PPG sensor and the second PPG sensor.

7. The sensor system as claimed in claim 1, further comprising applying baseline variation compensation to the PPG sensor output signal in advance of deriving the pulse amplitude variation value, the compensation being based on the derived baseline variation wherein the baseline variation compensation includes performing high-pass filtering.

8. The sensor system as claimed in claim 1, applying baseline variation compensation to the PPG sensor output signal in advance of deriving the pulse amplitude variation value, the compensation being based on the derived baseline variation, wherein the baseline variation compensation comprises for the or each PPG sensor, deriving a baseline variation of the or each PPG sensor output signal and processing the or each PPG sensor output signal to compensate for the derived baseline variation.

9. The sensor system as claimed in claim 7, wherein the adjustment step comprises both the applying baseline variation compensation and the combining a baseline variation of the PPG sensor output signal with the derived pulse amplitude variation value.

10. The sensor system as claimed in claim 1, wherein the combining the derived baseline variation with the derived pulse amplitude variation value comprises performing a linear combination of the derived baseline variation value with the derived pulse amplitude variation value.

11. The sensor system as claimed in claim 1, wherein the controller is adapted to derive a series of pulse amplitude variation values and a series of baseline variation values, and further adapted for the or each PPG sensor to apply a median filter to the pulse amplitude variation values and/or the baseline variation values from the PPG sensor output signal.

12. A method of deriving a modified pulse amplitude variation, comprising:
measuring a PPG signal;
deriving a baseline variation of the PPG signal;
deriving a pulse amplitude variation from the PPG signal; and
performing a post-adjustment step by which a modification is realized in the derived pulse amplitude variation based on the baseline variation of the PPG signal, wherein the post-adjustment step comprises:
subsequent to deriving the pulse amplitude variation, combining the derived baseline variation additively with the derived pulse amplitude variation to thereby generate the modified pulse amplitude variation.

13. The method as claimed in claim 12, further comprising:
measuring a second PPG signal;
generating a second modified pulse amplitude variation by:
deriving a second pulse amplitude variation from the second PPG signal, and performing a post-adjustment step by which modification is realized in the second derived pulse amplitude variation based on a derived baseline variation of the second PPG signal, the step comprising:
applying baseline variation compensation to the second PPG signal in advance of deriving the second pulse amplitude variation, based on the derived baseline variation of the second PPG signal; and/or
subsequent to deriving the second pulse amplitude variation, combining the derived baseline variation of the second PPG signal with the second derived pulse amplitude variation to thereby generate the second modified pulse amplitude variation; and
deriving an output pulse amplitude variation signal based on a combination of the modified pulse amplitude variations for the PPG sensor and the second PPG sensor.

14. A tangible, non-transitory computer readable medium that stores instructions, which when executed by a controller, cause the controller to:
process output signals from a photoplethysmography (PPG) sensor, the controller being adapted to generate a modified pulse amplitude variation value based on:

deriving a baseline variation of a PPG sensor output signal;

deriving a pulse amplitude variation value from the PPG sensor output signal; and performing a post-adjustment step by which modification is realized in the derived pulse amplitude variation value based on said baseline variation of the PPG sensor output signal, wherein the post-adjustment comprises:

subsequent to deriving the pulse amplitude variation value, combining the derived baseline variation additively with the derived pulse amplitude variation value to thereby generate the modified pulse amplitude variation value.

15. The tangible, non-transitory computer readable medium as claimed in claim 14, wherein the baseline variation is derived based on a variation in pulse maxima values of the PPG over time.

16. The tangible, non-transitory computer readable medium as claimed in claim 14, wherein the controller is further configured to process the PPG sensor output signal and a second PPG sensor output signal from another PPG sensor, the controller being further adapted to:

generate a second modified pulse amplitude variation value based on deriving a pulse amplitude variation value from the second PPG sensor output signal and performing said post-adjustment step in respect of the second derived pulse amplitude variation value based on a baseline variation of the second PPG sensor output signal to thereby realize a modification in the second pulse amplitude variation value; and derive an output pulse amplitude variation signal based on a combination of the modified pulse amplitude variation values for the PPG sensor and the second PPG sensor.

17. The tangible, non-transitory computer readable medium as claimed in claim 16, wherein the PPG sensor output signal is from a finger PPG sensor and the second PPG sensor output signal is from a forehead PPG sensor.

18. The tangible, non-transitory computer readable medium as claimed in claim 16, wherein the controller is adapted to derive an output pulse amplitude variation as a mean of the modified pulse amplitude variation values for the PPG sensor and the other PPG sensor.

19. The tangible, non-transitory computer readable medium as claimed in claim 14, applying baseline variation compensation to the PPG sensor output signal in advance of deriving the pulse amplitude variation value, the compensation being based on the derived baseline variation, wherein the baseline variation compensation includes performing high-pass filtering.

20. The tangible, non-transitory computer readable medium as claimed in claim 19, wherein the pre- or post-adjustment step comprises both the applying baseline variation compensation and combining a baseline variation of the PPG sensor output signal with the derived pulse amplitude variation value.

* * * * *